United States Patent [19]
Zimmon

[11] Patent Number: 5,980,468
[45] Date of Patent: Nov. 9, 1999

[54] APPARATUS AND METHOD FOR SERIAL COLLECTION STORAGE AND PROCESSING OF BIOPSY SPECIMENS

[75] Inventor: David S. Zimmon, Port Washington, N.Y.

[73] Assignee: Zimmon Scientific Corporation, Port Washington, N.Y.

[21] Appl. No.: 08/936,145

[22] Filed: Sep. 22, 1997

[51] Int. Cl.$^6$ .................................................. A61B 5/00
[52] U.S. Cl. ............................................................. 600/567
[58] Field of Search ...................... 600/564–567, 600/569, 572; 606/167, 170, 184

[56] References Cited

U.S. PATENT DOCUMENTS

| | | | |
|---|---|---|---|
| 3,515,128 | 6/1970 | McEvoy | 606/184 |
| 4,586,604 | 5/1986 | Alter | 600/569 |
| 4,803,998 | 2/1989 | Kezes et al. | 600/572 |
| 5,477,863 | 12/1995 | Grant | 600/572 |
| 5,538,008 | 7/1996 | Crowe | 600/564 |
| 5,542,432 | 8/1996 | Slater et al. | 600/564 |
| 5,562,100 | 10/1996 | Taylor | 128/751 |
| 5,573,008 | 11/1996 | Robinson et al. | 600/567 |
| 5,630,822 | 5/1997 | Hermann et al. | 606/114 |
| 5,649,547 | 7/1997 | Ritchart et al. | 600/566 |

FOREIGN PATENT DOCUMENTS

WO 93/04630  8/1992  WIPO .

*Primary Examiner*—Max Hindenburg
*Attorney, Agent, or Firm*—Collard & Roe, P.C.

[57] ABSTRACT

An apparatus and method for performing a medical procedure comprising an elongated member having an aperture extending longitudinally therethrough. The member has a proximal and an opposite distal end. An actuator is positioned within the aperture and has a proximal end and an opposite distal end. Biopsy means are connected to the distal end of the actuator for cutting and collecting biopsy specimens. Either the elongated member or the distal tip is modified to receive the cut specimens in the order of acquisition. After serial acquisition, the holding segment is separated from the remainder and closed by a cap to form a processing cassette. The cassette holds the specimens in the order of acquisition through fixation and processing to be opened for slicing or analysis.

21 Claims, 5 Drawing Sheets

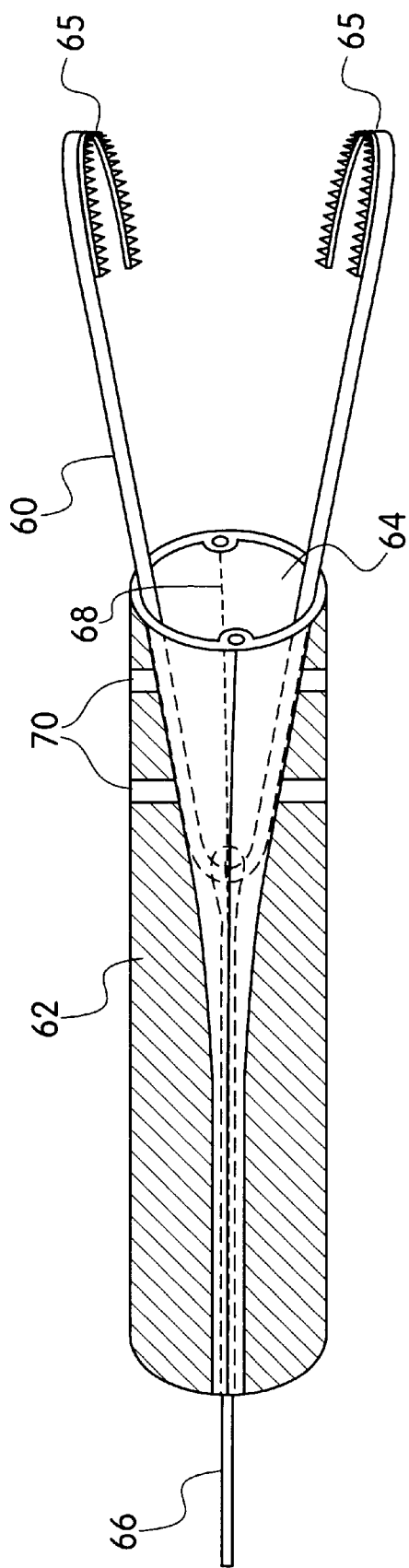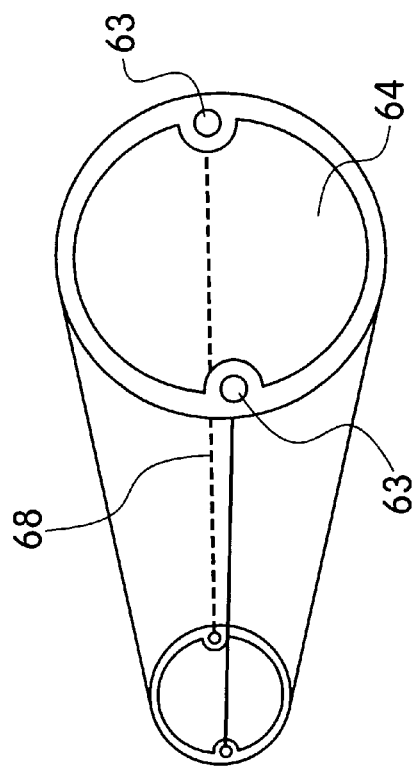

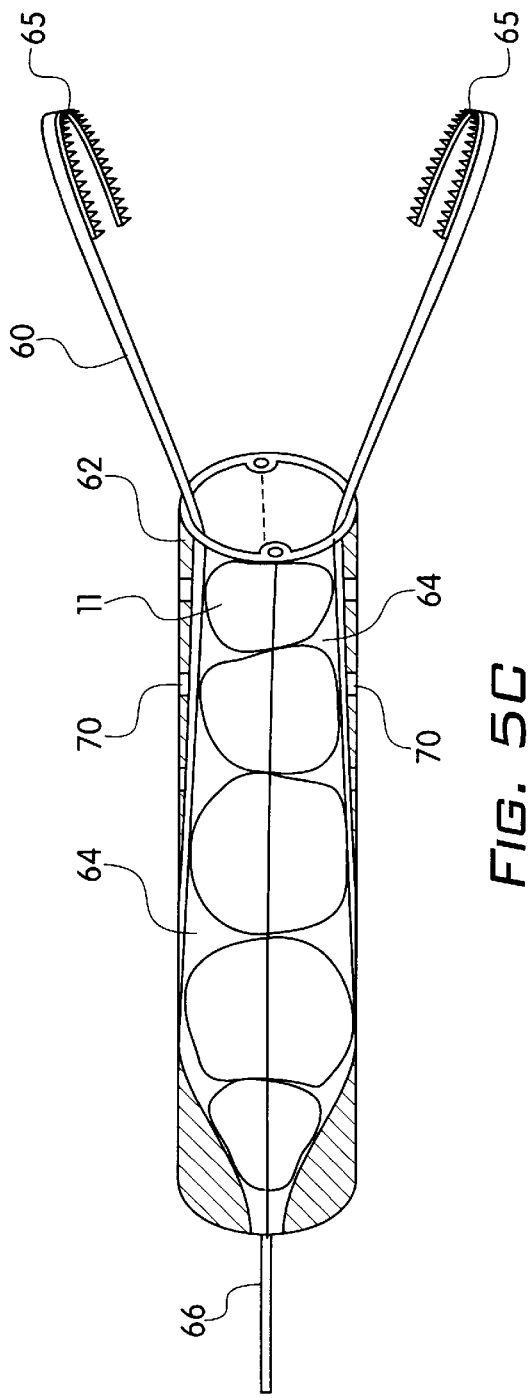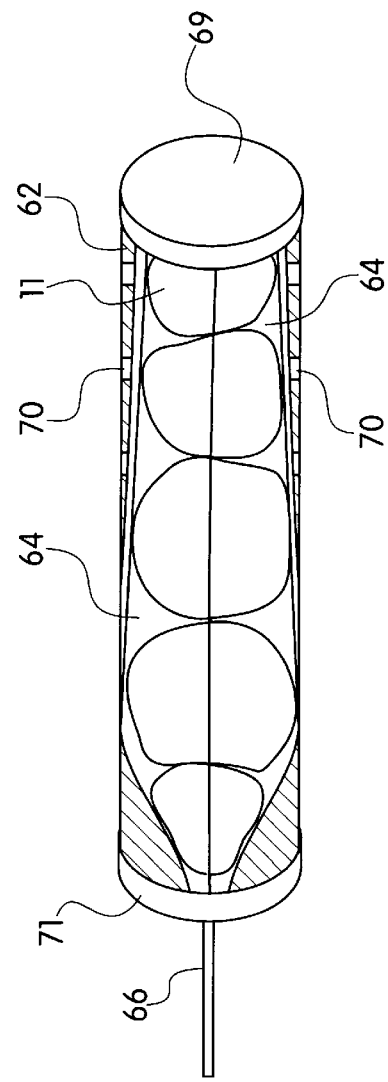

APPARATUS AND METHOD FOR SERIAL COLLECTION STORAGE AND PROCESSING OF BIOPSY SPECIMENS

BACKGROUND OF THE INVENTION

1. Field of the Invention

This invention relates generally to a method and devices for the serial collection, storage, and processing of biopsy specimens for microscopic, chemical, or other types of examination. In particular, the invention relates to biopsy sampling or removing tissue from any remote luminal structure within a patient, and storing the tissue within the removal apparatus in the order sampled through analysis or processing.

2. The Prior Art

It is often necessary to obtain tissue samples for examination from deep within luminal structures. These samples can only be retrieved by catheterization methods using endoscopic or fluoroscopic control, or by blind palpation. The biopsy devices used for these techniques remove 1 to 4 specimens that are retrieved by removing the biopsy instrument from the patient, and placing the specimen in a container of fixative solution labeled with the biopsy site and patient identification. The biopsies obtained in each pass are processed in a batch, since the minute pieces cannot be easily separated. Consequently, biopsies from different sites must be handled separately, thus requiring considerable effort and expense. The need to perform multiple biopsy passes because of the limited storage capacity of the biopsy instrument and the need to identify the sites of biopsy origin prolongs the procedure and may even cause it to fail, if the position of the biopsy instrument cannot be reacquired.

The batch of containers for each patient is then transported to the laboratory where the containers are serially opened and the specimens transferred to numbered cassettes that are recorded for later identification. The cassettes are then processed for examination. The processed specimens are then sliced, stained and mounted on labeled slides for microscopic examination. The specimens in each container must be processed separately to maintain identification. This is particularly important when the distribution and extent of a cancer is being mapped to determine the possibility of surgical removal and to prevent errors in reporting.

During this complex handling process, small specimens may be lost or damaged. At each stage of handling, the staff is exposed to possible infection from the biopsies particularly true when the unfixed specimen is removed from the sharp biopsy instrument before it is fixed. The staff is also exposed to solvent vapor from the fixative at each transfer step of processing. The solvents may be allergenic or carcinogenic. This tedious, labor intensive process is also expensive both in terms of time and laboratory space.

Although the prior art has made biopsy deep within the patient possible, the need for additional improvements remains. The present invention satisfies this need in a novel and unobvious way.

SUMMARY OF THE INVENTION

It is therefore an object of the present invention to provide a method and apparatus for the serial collection and storage of biopsies through the processing steps that overcomes the drawbacks of the prior art and allows the biopsies to be collected, stored and processed without excessive handling.

It is another object of the present invention to provide a method for the serial collection, storage and processing of biopsies that is simple to use and manufacture.

One embodiment of the present invention modifies biopsy instruments for capture of each biopsy serially and provides for storage within the biopsy instrument. The storage chamber is designed to be removed from the instrument shaft and closed to serve as a processing cassette without specimen handling, until the specimens are sliced for mounting and staining prior to microscopy, or analyzed chemically.

A device for obtaining tissue samples from remote locations within a patient according to one embodiment of the present invention comprises an elongated flexible member having a lumen, a distal end, and a proximal end. A cutting means is located near the distal end of the elongated member. The cutting means is actuated to cut tissue when the elongated member is moved toward the head or when the cutting distal head is moved toward the flexible member. An example of this type of device is shown in PCT Application WO 93/04630, the disclosure of which is herein incorporated by reference. The present invention modifies this device by providing storage means within the device and closing means for creating a cassette for storing and processing the specimens in the order they were collected. The cutting head serves as a packing means to force each biopsy into the shaft for storage.

Alternatively, the elongated member may serve as the cutting means and the head an anvil. Also, the biopsies can be stored within the head. The head is perforated to allow for fluid flow through the head. Each specimen is forced into the perforated head storage chamber by injecting fluid through the shaft before the cutting means and anvil are opened for the subsequent biopsy. The storage head containing the specimens is cut from the actuating shaft and closed with a perforated cap. The biopsy device head has now become a processing cassette with serial biopsies enclosed in order of acquisition, and ready for fixation and processing without further handling. In addition, the head can have a perforated flap that can be peeled open to allow for easy removal of the biopsy specimens. The cutting means can thus be located either on the head or the elongated member, and storage of the specimens can take place in either the head or the elongated member. Thus, four different permutations of this device are possible.

In a second embodiment of the present invention, a biopsy device for obtaining tissue samples from remote locations within a patient according to the invention comprises a flexible plastic catheter or shaft with one or two side lumens and a relatively large central lumen. The distal end contains a remotely controllable folded spring jaw biopsy device within the central lumen that is stabilized by metal or plastic guides. The guides enlarge the lumen and ensure that there is sufficient room to store the collected biopsy specimens as compared to a solid plastic extrusion with only a slot as a guide. It also enables the use of a simple extruded catheter for the device. In this embodiment, the folded spring jaw is extended proximally to form a chamber within the catheter to receive the specimens.

The junction of the chamber and the folded spring jaw is angulated to increase the distance between the jaws when they are extended and also to form a constriction at the distal most extent of the chamber. The actuator cable is biased to limit extension of the folded spring to the angled jaws distal to the constriction. The constriction and holding chamber remain within the catheter and prevent loss of the stored biopsies. As the spring jaws are drawn into the catheter with each new biopsy, the constriction is reduced, allowing the latest specimen to be aspirated into the holding chamber. The side lumen(s) have open slits to carry suction from the proximal end of the catheter to draw the specimens into the chamber after each biopsy.

The distal end of the apparatus is capped after withdrawal. The catheter is cut at a marked site proximal to the specimen holding chamber and capped with a second cap. Perforated caps allow fixation and processing of the specimens within the chamber. The catheter has thus become a processing cassette with the serial specimens enclosed in order of acquisition and ready for fixation and processing without further handling. Plastic or metal guides are preferably inserted into the central lumen of the catheter to support and prevent twisting of the folded spring and to create a chamber for the storage of biopsies.

After processing to wax, the closed shaft is cut open and the biopsies are ready for slicing, still remaining in order of acquisition. Thus, a single log prepared at the time of biopsy serves to identify each specimen to the submitter and laboratory, and for reporting without handling, risk of biopsy loss or documentation error.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 5A is a sectional view of an alternative embodiment of the device showing a spring-based biopsy retrieval and collection device according to the invention;

FIG. 5B is a perspective view showing the distal suction slits as extensions of the side hole extrusions of the embodiment shown in FIG. 5A;

FIG. 5C is a sectional view of the embodiment shown in FIG. 5A with the biopsy specimen chamber filled and the biopsy jaws extended; and FIG. 5D is a sectional view of the device shown in FIG. 5C showing the perforated caps in place after removing the shaft and jaws.

DETAILED DESCRIPTION OF THE PREFERRED EMBODIMENTS

Figure 1A:
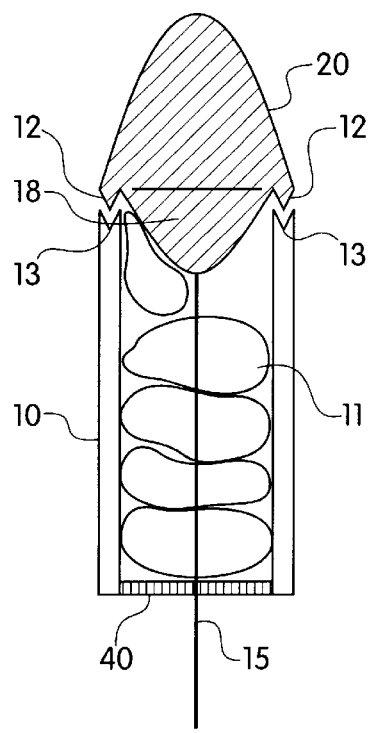
FIG. 1A is a sectional view of one embodiment of the lateral biopsy device with the head operating as cutting blade and packing device.

For the purposes of promoting an understanding of the principles of the invention, reference will now be made to the embodiments illustrated in the drawings and specific language will be used to describe same. It will nevertheless be understood that no limitation of the scope of the invention is thereby intended, such alterations and further modifications in the illustrated device, and such further applications of the principles of the invention as illustrated therein being contemplated as would normally occur to one skilled in the area to which the invention relates.

With reference to FIGS. 1 through 4, there is illustrated several embodiments of the device according to the invention, which permits serial specimen collection, storage and processing. As shown in FIG. 1A, a biopsy obtained with this method is cut as blade 12 approaches anvil 13. Therefore, the distance between blade 12 and anvil 13, which is determined by the distance moved by actuator cable 15, is the major determinant of specimen length. Biopsy width is constrained by actuator cable 15 to approximately 50% of the diameter of cutting blade 12. Within areas of narrowing, specimen 11 is forced into the cutting chamber and cannot escape except into either the receptacle head, shown in FIGS. 3A-3B and 4A-4C, or shaft shown in FIGS. 1A, 1B and 2. These external constraints, combined with a conical packing shaft 18 within the head 20, provide the force to align, pack, and maintain specimen position as well as prevent loss of the specimen 11 when shaft 10 and head 20 are drawn apart for additional biopsies.

When the device according to the invention is used within an unconstrained space, the force to align, pack, and store the biopsies must be provided by the instrument itself. In this circumstance, biopsy size is important and a minimum specimen length of twice the blade diameter is assumed to align specimens within the storage space and prevent mixing. This is provided by calibrating shaft movement to that minimum distance. Packing of specimen 11 into shaft 10 and prevention of loss is accomplished by conical packing shaft 18 attached to cutting head 20 that extends into shaft 10 so that packed specimens are constrained.

Figure 2:
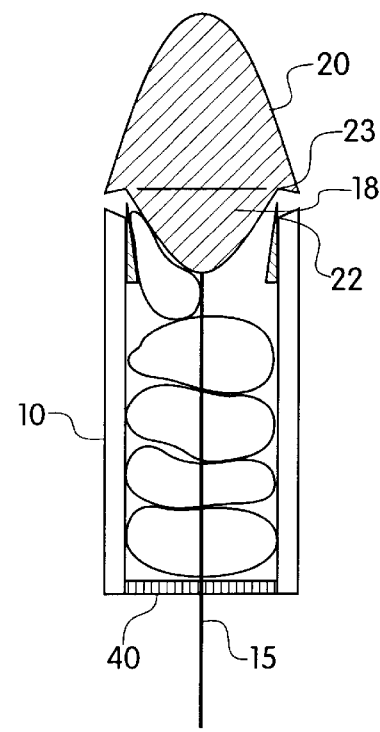
FIG. 2 is a sectional view of the device according to the invention showing the blade operating from the catheter shaft with the shaft as the specimen storage site.
Figure 1B:
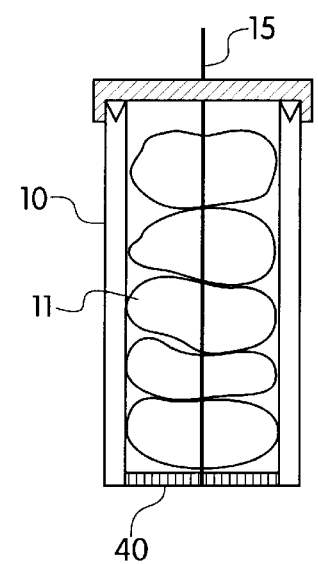
FIG. 1B is a sectional view after removal of the cutting head and placement of a perforated cap.

The procedure described above allows the operator to collect and store the specimens in the sequence of acquisition, and allows hands-off processing of the specimens without loss of sequence. The lateral biopsy device provides for either a cutting head, shown in FIG. 1A, or cutting shaft, shown in FIG. 2. Either of these parts may be used as the receptacle for serial specimens that may then be processed in situ. Each option has distinct advantages and disadvantages that will be made clear by the following:

FIGS. 1A, 1B and 2 show examples of the device according to the invention wherein storage of biopsy specimens 11 is in the shaft 10. Shaft storage has the advantage of great storage space in relation to the length of the cutting head without altering operating characteristics of the biopsy device. This option permits retrieval of many samples and a large specimen volume using device diameters of 5F or smaller where head length is limited to 3 times shaft diameter by the need to traverse narrow tortuous pathways. As shown in FIG. 1A, the cutting blade is on the head, and collection of specimens 11 proceeds by bringing blade 12 down onto anvil 13 by tension on wire 15. Blade 12 cuts specimen 11, which is then drawn down into shaft 10. Packing head 18 serves to compress specimens 11 further into shaft 10. Wire 15 also compresses specimens 11 within shaft 10.

A stopper 40 is placed within shaft 10 and connected to wire 15. Stopper 40 is preferably perforated and serves as an end point to the storage chamber formed by shaft 10.

After the desired number of specimens 11 has been collected and the instrument removed from the patient's body, head 20 is removed from shaft 10. Wire 15 is cut and led through a perforated cap 30, which is placed over the open end of shaft 10, as shown in FIG. 1B. Wire 15 is then pulled from cap 30 to raise stopper 40 and compress specimens 11 within shaft 10.

FIGS. 1A and 1B show a perforated stopper 40 that limits the movement of specimens 11 up shaft 10, determines the length of the storage space, number of biopsies that can be stored, and provides a proximal cap after shaft 10 is cut. The distal perforated cap 30 is also shown in FIG. 1B. The application of both stopper 40 and cap 30 provides a sealed storage cassette for specimens 11.

If the initial distance between stopper 40 and the end of shaft 10 where cap 30 is placed is known, the length of the shaft containing the biopsies to be processed can be determined by measuring the length of wire outside the cap after the wire is pulled through the cap. Shaft 10 can then be cut to this length to create a compact processing cassette for specimens 11. The perforated cap 30 and stopper 40 allow for exposure of specimens 11 during storage and processing.

In an alternative embodiment shown in FIG. 2, the cutting blade 22 is on shaft 10 instead of in head 20. Cutting blade 22 cuts specimens 11 when head 20 containing anvil 23 is brought down onto blade 22. Packing head 18 compresses specimens 11 into shaft 10 for storage. Placement of cap 30 and further compression of specimens 11 proceeds as with the device shown in FIGS. 1A and 1B, above.

Figure 3A:
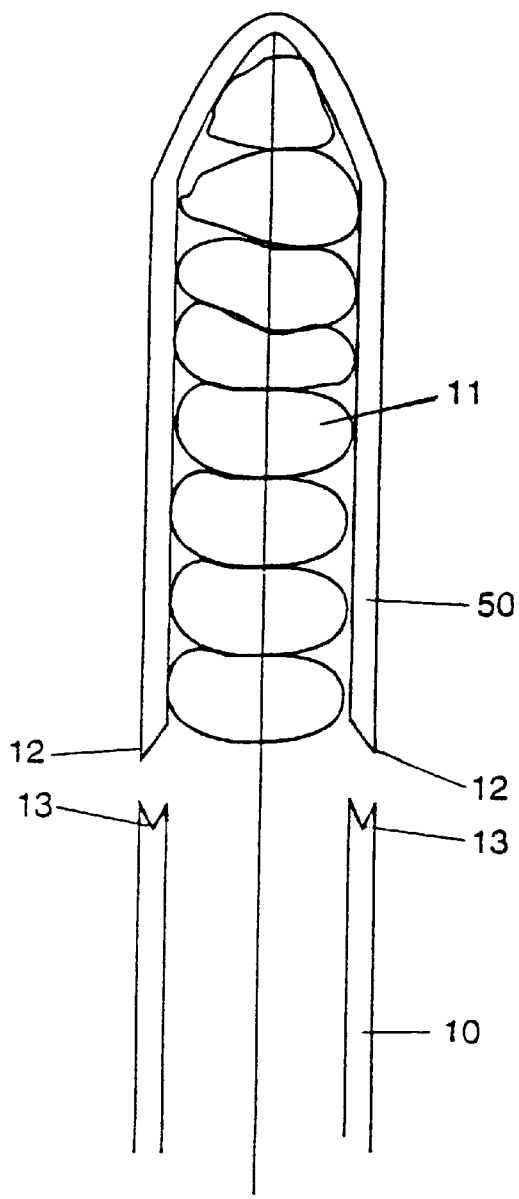
FIG. 3A is a sectional view of another embodiment of the device according to the invention where the cutting head is the specimen storage area.
Figure 3B:
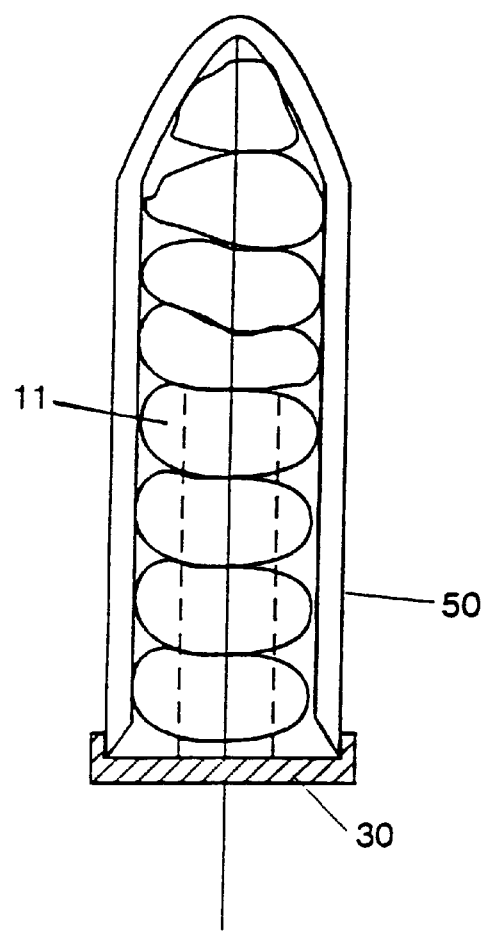
FIG. 3B is a sectional view of the device shown in FIG. 3A showing the specimen filled head after capping.

In an alternative embodiment, specimens 11 can be stored in head 50, as shown in FIGS. 3 and 4. FIGS. 3A and 3B show the device according to the invention, wherein head 50 is hollow and serves as the storage chamber for specimens 11. Similar to the device shown in FIG. 1A, cutting blade 12 is located on head 50, and serves to cut specimens 11 when it is brought down onto anvil 13.

As shown in FIGS. 3A and 3B, cutting head 50 is a cylindrical space made of metal or plastic with a proximal facing blade. If the head is hollow, cut specimens may be stored within this space. The headspace has a direct relationship to its diameter, length and the size of the sample. The head diameter must conform to the shaft diameter. Head length is limited by the rigidity produced by head length that impedes maneuverability of the device. Head length must be limited, generally, to between 2 and 4 times shaft diameter to allow easy passage of the device around curves in the endoscope or passage that is to be traversed. The possibility of special cases remains.

As the biopsy is proportional to shaft and head diameter, and the headspace must be limited to align the sequential stored biopsies. In one preferred embodiment, the catheter is 7 French or 2.3 mm in diameter, with a head length twice the diameter of the shaft of 4.6 mm, will only store 5-6 specimens. Increasing head length to 3 times diameter or 7 mm increases storage capacity to 10. Further increases in head length to 4, 5, or 6 times the shaft diameter increases biopsy storage capacity to 13, 16, and 20 specimens, respectively, but at the cost of a longer rigid tip that progressively prevents accurate positioning and limits maneuverability.

Head 50 is preferably perforated to allow for packing of the specimens 11 within head 50 by injecting fluid through shaft 10 into head 50. The fluid pressure causes specimens 11 to be compressed into head 50 and the fluid can then escape through perforated head 50.

When the desired number of specimens 11 have been collected in head 50, wire 15 is cut and cap 30 is placed over the opening in head 50 to enclose specimens 11. Cap 30 is preferably perforated to allow the addition of fixative to specimens 11. Alternatively, a tube of plastic screen can be placed within the hollow head 50, which is then closed on either end with a packing disc and removal plate. The screen can then be removed from head 50 for further processing and storage of specimens 11.

Figure 4A:
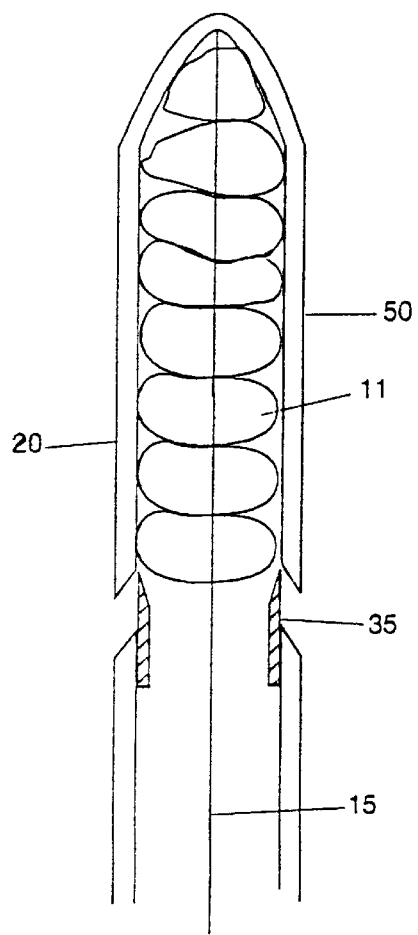
FIG. 4A is a sectional view of an alternative embodiment of the device according to the invention showing the blade operating from the shaft with the head as the specimen storage site.

In another alternative embodiment, the blade 35 can be located on shaft 10 and the specimens 11 stored in head 50, as shown in FIG. 4a. After collection of specimens 11, wire 15 is cut and cap 30 is placed over the open end of head 50, as shown in FIG. 4B.

Figure 4B:
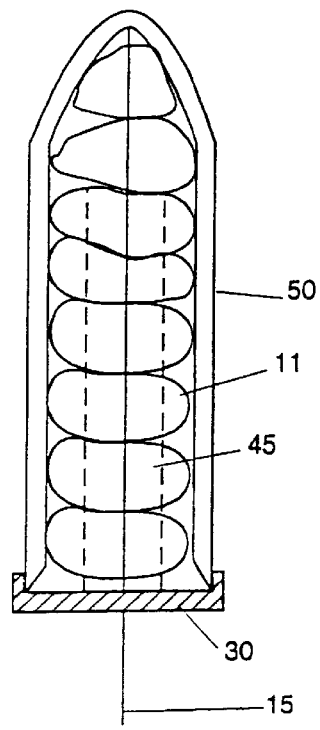
FIG. 4B is a sectional view showing the head of FIG. 4A with a cap.
Figure 4C:
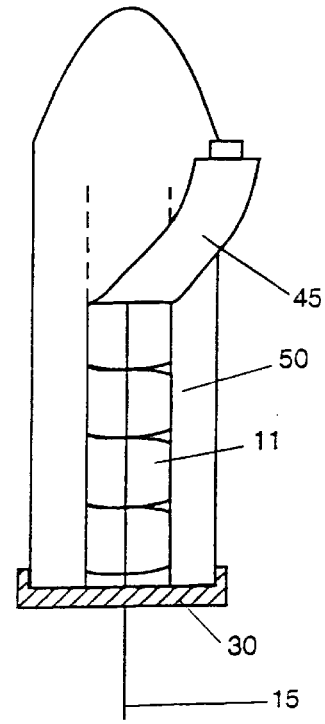
FIG. 4C is a side view of the head of FIG. 4b, showing the perforated flap being peeled away.

As shown in FIG. 4B, head 50 preferably has a perforated flap 45 formed therein, which can be peeled open to release specimens 11 from head 50 for further processing, as shown in FIG. 4C.

In yet another alternative embodiment, as shown in FIGS. 5A–5D, the device retrieves specimens 11 through a spring-based biopsy cutting tool 60. Cutting tool 60 is arranged inside a catheter 62, which has two small side lumens 63 and a large central lumen 64. Central lumen 64 has a plurality of jaw guides 70 which act as a specimen holding chamber, as shown in FIGS. 5C and 5D. Jaw guides 70 could be made of any suitable material such as metal or plastic. Cutting tool 60 has two spring-based jaws equipped with two open-faced cutting blades 65 on each jaw of cutting tool 60.

Cutting tool 60 is deployed to cut and retrieve biopsy specimens, and to bring the specimens inside catheter 62 for storage. The movement of tool 60 is controlled by actuator wire 66, which, when pulled, causes the tool 60 to retract and blades 65 to come together to cut specimen 11. Further pulling on wire 66 causes tool 60 to retract inside lumen 64 and pull specimen 11 inside as well. After specimen 11 is deposited inside lumen 64, tool 60 can then be deployed to cut and retrieve additional specimens.

Side lumens 63 are connected to lumen 64 through a plurality of slits 68. Suction can be applied to side lumens 63 at the proximal end of catheter 62, which is then carried into central lumen 64 through slits 68 to draw specimens 11 into central lumen 64 after each biopsy.

When the desired number of specimens 11 have been collected, tool 60 is removed from catheter 62 and the distal end is capped with a perforated cap 69, as shown in FIG. 5D. Perforated cap 69 allows for addition of fixative to the specimens during storage in lumen 64. Catheter 62 is then cut at a specified site at its proximal end and capped with a cap 71, thus creating a processing cassette whereby the specimens can be processed in order of acquisition without the preparation of additional logs or excessive handling of specimens 11.

While several embodiments of the present invention have been shown and described, it is to be understood that many changes and modifications may be made thereunto without departing from the spirit and scope of the invention as defined in the appended claims.

What is claimed is:

1. An apparatus for performing a medical procedure, comprising:
    an elongated flexible member having an aperture extending longitudinally therethrough, said member having a proximal and an opposite distal end and a portion that is separable from said flexible member;
    an actuator positioned within the aperture, said actuator having a proximal end and an opposite distal end;
    biopsy means connected to the distal end of the actuator for cutting and collecting biopsy specimens; and
    a cap positionable over said separable portion when said portion is removed from the flexible member, said cap closing said portion for storage and processing of biopsy specimens collected by the biopsy means in the order of collection.

2. An apparatus according to claim 1, wherein the elongated member comprises a catheter and the biopsy means comprises:
 a rounded head attached to the distal end of said actuation means;
 a cutting edge attached to one of said catheter and said head; and
 a cutting surface attached to the other of said catheter and said head, said cutting means being actuated to cut tissue when said head is moved with respect to said catheter by said actuator.

3. An apparatus according to claim 2, wherein the head is hollow and the cap closes the head.

4. An apparatus according to claim 3, wherein the head has a length of between 2 and 4 times the diameter of the elongated member.

5. An apparatus according to claim 2, wherein the cap seals the catheter for storage and processing of biopsy specimens within the catheter.

6. An apparatus according to claim 5, further comprising a conical packing shaft on the head and extending into the catheter for packing, aligning and maintaining the position of collected biopsy specimens within the catheter.

7. An apparatus according to claim 2, wherein the actuator comprises a wire, and further comprising a stopper attached to the wire at a predetermined position, to define a storage compartment between the cap and the stopper for the biopsy specimens.

8. An apparatus according to claim 7, wherein the wire is pulled out from the cap and fixed to compress the specimens within the apparatus.

9. An apparatus according to claim 8, wherein the catheter is cut proximal to the stopper to form a capsule for the collected specimens.

10. An apparatus according to claim 3, wherein the head is perforated to allow packing of biopsy specimens by fluid injected through the catheter and permeation by fluid for fixation and processing.

11. An apparatus according to claim 2, wherein the head has a perforated flap that is peelably opened for removal of the biopsy specimens.

12. An apparatus according to claim 1, wherein the cap is perforated.

13. An apparatus according to claim 1, wherein the biopsy means comprises a spring jaw having a cutting tool, said spring jaw being remotely deployable from said flexible member, and an internal jaw guide in the distal end of said member, said jaw guide contacting along said jaw for controlling the precise movement of said jaw and defining a cavity within said member for receiving a substantial portion of said jaw.

14. An apparatus according to claim 13, wherein the member is a catheter and the spring jaw and jaw guide are elongated to form a chamber within the catheter for serial acquisition, storage and processing of specimens within the chamber.

15. An apparatus according to claim 14, wherein the catheter is a plastic extrusion having a large central lumen and two smaller side lumens.

16. An apparatus according to claim 15, wherein the side lumens are connected via slits to the central lumen and act as a suction means to draw the biopsy specimens into the chamber in order of acquisition after each biopsy.

17. An apparatus according to claim 16, wherein the cap is perforated, and the catheter is cut proximal to the chamber and closed with the cap.

18. An apparatus according to claim 13, further comprising a second cap for closing the distal end of the flexible member after collection of biopsies.

19. A method for the serial collection, storage and processing of biopsy specimens, comprising
 cutting at least one specimen with a biopsy means deployed from an elongated hollow member;
 placing said specimen within said elongated hollow member in order of collection;
 removing said biopsy means from said elongated member; and
 closing said elongated member with at least one perforated cap, to create a processing cassette for said specimens.

20. The method according to claim 19, further comprising compressing said specimens within said elongated hollow member and cutting said member to create a compact processing cassette.

21. A method for the serial collection, storage and processing of biopsy specimens, comprising
 cutting at least one specimen with a biopsy means on an apparatus having a hollow head;
 placing said specimen within said hollow head in order of collection;
 removing the hollow head from the apparatus; and
 closing the hollow head with a perforated cap to create a processing cassette for said specimens.

* * * * *